(12) United States Patent
Hauck

(10) Patent No.: US 7,187,973 B2
(45) Date of Patent: *Mar. 6, 2007

(54) CONGESTIVE HEART FAILURE PACING OPTIMIZATION METHOD AND DEVICE

(75) Inventor: John A. Hauck, Shoreview, MN (US)

(73) Assignee: Endocardial Solutions, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/295,358

(22) Filed: Nov. 15, 2002

(65) Prior Publication Data

US 2003/0120318 A1   Jun. 26, 2003

Related U.S. Application Data

(60) Continuation-in-part of application No. 09/588,930, filed on Jun. 7, 2000, now Pat. No. 6,603,996, and a continuation-in-part of application No. 09/589,387, filed on Jun. 7, 2000, and a continuation-in-part of application No. 09/589,322, filed on Jun. 7, 2000, now abandoned, and a continuation-in-part of application No. 09/107,371, filed on Jun. 30, 1998, which is a division of application No. 08/387,832, filed as application No. PCT/US93/09015 on Sep. 23, 1993, now Pat. No. 6,240,307, which is a continuation of application No. 07/950,448, filed on Sep. 23, 1992, now Pat. No. 5,297,549, which is a continuation-in-part of application No. 07/949,690, filed on Sep. 23, 1992, now Pat. No. 5,311,866.

(51) Int. Cl.
*A61N 1/18* (2006.01)

(52) U.S. Cl. .................... 607/17; 128/898; 607/122
(58) Field of Classification Search ............... 600/324, 600/374; 606/73; 128/898; 607/17, 122–3
See application file for complete search history.

(56) References Cited

U.S. PATENT DOCUMENTS

| | | | |
|---|---|---|---|
| 4,173,228 A | | 11/1979 | Van Steenwyk et al. |
| 4,313,442 A | * | 2/1982 | Knudson et al. .............. 607/17 |
| 4,431,005 A | | 2/1984 | McCormick |
| 4,478,223 A | | 10/1984 | Allor |
| 4,613,866 A | | 9/1986 | Blood |
| 4,697,595 A | | 10/1987 | Breyer et al. |
| 4,699,147 A | | 10/1987 | Chilson et al. |
| 4,821,731 A | | 4/1989 | Martinelli et al. |

(Continued)

OTHER PUBLICATIONS

Arisi, G., et al., "Localization Of Ectopic Ventricular Focuses By Means Of A Diameter Multielectrode Catheter," *Advances in Electrocardiology*, Elsevier Science Publishers B.V. (Biomedical Division), Z. Antaloczy et al., editors, pp. 67-70 (1990).

(Continued)

*Primary Examiner*—Roy D. Gibson
*Assistant Examiner*—Pete Vrettakos
(74) *Attorney, Agent, or Firm*—Sterne, Kessler, Goldstein & Fox, P.L.L.C.

(57) ABSTRACT

Conduction volumetry is used to determine the hemodynamic performance of the heart under various pacing protocols to optimize cardiac output as a function of the pacing protocol.

1 Claim, 6 Drawing Sheets

U.S. PATENT DOCUMENTS

| | | | |
|---|---|---|---|
| 4,898,181 A | 2/1990 | Kessler | |
| 4,945,305 A | 7/1990 | Blood | |
| 5,042,486 A | 8/1991 | Pfeiler et al. | |
| 5,054,492 A | 10/1991 | Scribner et al. | |
| 5,054,496 A | 10/1991 | Wen et al. | |
| 5,056,517 A | 10/1991 | Fenici | |
| 5,081,993 A | 1/1992 | Kitney et al. | |
| 5,158,092 A | 10/1992 | Glace | |
| 5,161,536 A | 11/1992 | Vilkomerson et al. | |
| 5,211,165 A | 5/1993 | Dumoulin et al. | |
| 5,220,924 A | 6/1993 | Frazin | |
| 5,228,442 A | 7/1993 | Imran | |
| 5,273,038 A | 12/1993 | Beavin | |
| 5,295,484 A | 3/1994 | Marcus et al. | |
| 5,305,745 A * | 4/1994 | Zacouto | 600/324 |
| 5,323,781 A | 6/1994 | Ideker et al. | |
| 5,324,284 A | 6/1994 | Imran | |
| 5,325,860 A | 7/1994 | Seward et al. | |
| 5,372,138 A | 12/1994 | Crowley et al. | |
| 5,377,678 A | 1/1995 | Dumoulin et al. | |
| 5,385,146 A | 1/1995 | Goldreyer | |
| 5,391,199 A | 2/1995 | Ben-Haim | |
| 5,433,198 A | 7/1995 | Desai | |
| 5,553,611 A * | 9/1996 | Budd et al. | 600/374 |
| 5,558,091 A | 9/1996 | Acker et al. | |
| 5,588,432 A | 12/1996 | Crowley | |
| 5,662,108 A * | 9/1997 | Budd et al. | 600/374 |
| 5,687,737 A | 11/1997 | Branham et al. | |
| 5,713,363 A | 2/1998 | Seward et al. | |
| 5,738,096 A | 4/1998 | Ben-Haim | |
| 5,840,031 A | 11/1998 | Crowley | |
| 6,004,269 A | 12/1999 | Crowley et al. | |

OTHER PUBLICATIONS

Branham B., et al., "A System For Accurate Interactive 3-D Display Of Cardiac Electrical Activity," *Computers in Cardiology*, IEEE Computer Society Press 0276-6547/92, pp. 335-338 (Oct. 11-14, 1992).

Breyer, B. and Cikes, I., "Ultrasonically Marked Catheter—A Method For Positive Echographic Catheter Position Identification," *Med. & Biol. Eng. & Comput.*, 22:268-271 (May 1984).

Buckles, D., et al. "Computer-Enhanced Mapping Of Activation Sequences In The Surgical Treatment Of Supraventricular Arrhythmias," *PACE*, vol. 13, Part I, pp. 1401-1407 (Nov. 1990).

Cikes, I., et al., "Cardiac Catheterisation Guided By Ultrasound," *Journal of the American College of Cardiology*, vol. 3, No. 2, p. 564 (Feb. 1984).

Cikes, I. and Breyer, B., "Complete Cardiac Catherisation Guided By Ultrasound," *European Heart Journal*, vol. 4, (suppl. E), p. 21 (1983).

Cikes I., "Interventional Echocardiography," *5th Symposium on Echocardiology*, Rotterdam, Abstracts p. 38 (1983).

Cikes, I., et al., "Interventional Echocardiography," *Interventional Ultrasound*, 1st edition, chapter 25, Munksgaard, Copenhagen, pp. 160-168 (1985).

Cox, J., et al., "Surgery For Atrial Fibrillation," *Cardiac Surgery: State of the Art Reviews*, vol. 4, No. 1, pp. 207-217 (1990).

De Bakker, J., et al., "Endocardial Mapping By Simultaneous Recording Of Endocardial Electrograms During Cardiac Surgery For Ventricular Aneurysm," *Journal of American College of Cardiology*, vol. 2, No. 5, pp. 947-953 (Nov. 1983).

Derfus, D. and Pilkington, T., "Assessing The Effect Of Uncertainty In Intracavitary Electrode Position On Endocardial Potential Estimates," *IEEE Transactions on Biomedical Engineering*, vol. 39, No. 7, pp. 676-681 (Jul. 1992).

Derfus, D., et al., "Calculating Intracavitary Potentials from Measured Endocardial Potentials," *Annual International Conference of the IEEE Engineering in Medicine and Biology Society*, vol. 12, No. 2, p. 635 (1990).

Derfus, D., et al., "A Comparison of Measured and Calculated Intracavitary Potentials for Electrical Stimuli in the Exposed Dog Heart," *IEEE Transactions on Biomedical Engineering*, vol. 39, No. 11, pp. 1192-1206 (Nov. 1992).

Derfus, D. and Pilkington, T., "Effect Of Intracavitary Electrode Position On Endocardial Potential Estimates," *IEEE Engineering in Medicine & Biology Society 10th Annual International Conference*, pp. 185-186 (1988).

Desai, J., et al., "Orthogonal Electrode Catheter Array for Mapping of Endocardial Focal Site of Ventricular Activation," *PACE*, vol. 14, Part I, pp. 557-574 (Apr. 1991).

Downar, E., et al., "Endocardial Mapping of Ventricular Tachycardia in the Intact Human Ventricle: Evidence for Reentrant Mechanisms," *Journal of the American College of Cardiology*, vol. 11, No. 4, pp. 783-791 (Apr. 1988).

Durrer, D. and Van Der Tweel, L., "Spread of Activation in the Left Ventricular Wall of the Dog. II.: Activation Conditions at the Epicardial Surface," *American Heart Journal*, pp. 192-203 (Aug. 1953).

Fann, J., et al., "Endocardial Activation Mapping and Endocardial Pace-Mapping Using a Balloon Apparatus," *Am. J. Cardiol.*, vol. 55, pp. 1076-1083 (1985).

Fenici, R. and Melillo, G., "Biomagnetically Localizable Multipurpose Catheter And Method For MCG Guided Intracardiac Electrophysiology, Biopsy And Ablation Of Cardiac Arrhythmias," *International Journal of Cardiac Imaging*, vol. 7, pp. 207-215 (1991).

Fenici, R., et al., "Catheter Ablation Of Cardiac Arrhythmias: Magnetocardiographic Localization Of Electrocathters And Arrhythmogenic Foci," *8th International Congress "The New Frontiers of Arrhythmias,"* Marilleva, Italy, pp. 723-731 (Jan. 31-Feb. 6, 1988).

Fenici, R., et al., "Clinical Magnetocardiography: 10 Years Experience At The Catholic University," *International Journal of Cardiac Imaging*, vol. 7, pp. 151-167 (1991).

Fenici, R. and Melillo, G., "Magnetocardiography: Ventricular Arrhythmias," *European Heart Journal*, vol. 14 (Suppl. E), pp. 53-60 (1993).

Harada, A., et al., "Potential Distribution Mapping: New Method For Precise Localization Of Intramural Septal Origin Of Ventricular Tachycardia," *Circulation*, vol. 78 (Suppl. III), No. 5, pp. III-137-III-147 (Nov. 1988).

Hauer, R., et al., "Endocardial Catheter Mapping: Validation Of A Cineradiographic Method For Accurate Localization Of Left Ventricular Sites," *Circulation*, vol. 74, No. 4, pp. 862-868 (Oct. 1986).

Hauer, R., et al., "Endocardial Catheter Mapping: Wire Skeleton Technique For Representation Of Computed Arrhythmogenic Sites Compared With Intraoperative Mapping," *Circulation*, vol. 74, No. 6, pp. 1346-1354 (Dec. 1986).

Ideker, R., et al., "A Computerized Method For The Rapid Display Of Ventricular Activation During The Intraoperative Study Of Arrhythmias," *Circulation*, vol. 59, No. 3, pp. 449-458 (Mar. 1979).

Ideker, R., et al., "Simultaneous Multichannel Cardiac Mapping Systems," *PACE*, vol. 10, pp. 281-292 (Mar.-Apr. 1987).

Ideker, R., "A Study To Evaluate The Ability Of A Multielectrode Intracavitary Probe To Determine The Site Of Origin Of Ventricular Tachycardia," *Basic Arrhythmia Laboratory, Engineering Research Center in Emerging Cardiovascular Technologies*, Duke University, pp. 1-3.

Jackman, W., et al., "New Catheter Technique For Recording Left Free-Wall Accessory Atrioventricular Pathway Activation: Identification Of Pathway Fiber Orientation," *Circulation*, vol. 78, No. 3, pp. 598-611 (Sep. 1988).

Josephson, M., *Clinical Cardiac Electrophysiology: Techniques and Interpretations*, 2nd ed., pp. 566-580, 608-615, and 770-783 (1993).

Josephson, M., et al., "Comparison Of Endocardial Catheter Mapping With Intraoperative Mapping Of Ventricular Tachycardia," *Circulation*, vol. 61, No. 2, pp. 395-404 (Feb. 1980).

Josephson, M., et al., "Role Of Catheter Mapping In Evaluation Of Ventricular Tachycardia," *Ventricular Tachycardia—Mechanisms And Management*, pp. 309-330, Mt. Kisco, NY: Futura Publishing Co. (1982).

Josephson, M., et al., "Role Of Catheter Mapping In The Preoperative Evaluation Of Ventricular Tachycardia," *American Journal of Cardiology*, vol. 40, pp. 207-220 (Jan. 1982).

Josephson, M., et al., "Ventricular Activation During Ventricular Endocardial Pacing. II. Role Of Pace-Mapping To Localize Origin Of Ventricular Tachycardia," *The American Journal of Cardiology*, vol. 50, pp. 11-22, (Jul. 1982).

Kaltenbrunner, W., et al., "Epicardial And Endocardial Mapping Of Ventricular Tachycardia In Patients With Myocardial Infarction: Is The Origin Of The Tachycardia Always Subendocardially Localized?," *Circulation*, vol. 84, No. 3, pp. 1058-1071 (Sep. 1991).

Khoury, D. and Rudy, Y., "A Model Study Of Volume Conductor Effects On Endocardial And Intracavitary Potentials," *Circulation Research*, vol. 71, No. 3, pp. 511-525 (Sep. 1992).

Khoury, D. and Rudy, Y., "Reconstruction Of Endocardial Potentials From Intracavitary Probe Potentials: A Model Study," IEEE 0276-6547/92, pp. 9-12 (1992).

Kun, S. and Peura, R., "Conductance Volumetric Model Of An Eccentrically Positioned Catheter Within A Three-Compartment Ellipsoidal Ventricle," *IEEE Transactions on Biomedical Engineering*, vol. 40, No. 6, pp. 589-592 (Jun. 1993).

Langberg, J., et al., "The Echo-Transponder Electrode Catheter: A New Method For Mapping The Left Ventricle," *Journal of the American College of Cardiology*, vol. 12, pp. 218-223 (Jul. 1988).

Laxer, C., et al., "A Graphical Display System For Animating Mapped Cardiac Potentials," *Third Annual IEEE Symposium on Computer-Based Medical Systems*, IEEE Computer Society, pp. 197-204 (1990).

Lu, S. and Eiho, S., "Compound 3-D Visualization Of Reconstructed Coronary Arteries, Left Ventricle And Aorta From Biplane X-Ray Angiograms," *Computers in Cardiology*, IEEE Computer Society Press, 0276-6547/92, pp. 535-538 (Oct. 11-14, 1992).

Macchi, E., et al., Intracavitary Mapping: An Improved Method For Locating The Site Of Origin Of Ectopic Ventricular Beats By Means Of A Mathematical Model, *IEEE Engineering in Medicine & Biology Society 10th Annual International Conference*, pp. 0187-0188 (1988).

Macchi, E., et al., "Localization Of Ventricular Ectopic Beats From Intracavitary Potential Distributions: An Inverse Model In Terms Of Sources," *IEEE Engineering in Medicine & Biology Society 11th Annual International Conference*, pp. 0191-0192 (1989).

Masse, S., et al., "A Three-Dimensional Display For Cardiac Activation Mapping," *PACE*, vol. 14, Part I, pp. 538-545 (Apr. 1991).

Moshage, W., et al., "Biomagnetic Localization Of Ventricular Arrhythmias," *Radiology*, vol. 180, No. 3, pp. 685-692 (Sep. 1991).

Moura, L., et al., "A Microcomputer-Based Cardiac Mapping System For Recurrent Ventricular Tachycardia Surgery," *Computers in Cardiology* IEEE Computer Society Press, 0276-6547/92, pp. 431-434 (Oct. 11-14, 1992).

Pagé, P., et al., "Surgical Treatment Of Ventricular Tachycardia: Regional Cryoablation Guided By Computerized Epicardial And Endocardial Mapping," *Circulation*, vol. 80 (Suppl. I), No. 3, pp. I-124-I-134 (Sep. 1989).

Pilkington, T., et al., "Feasibility Of Estimating Endocardial Potentials From Cavity Potentials," *IEEE Ninth Annual Conference of the Engineering in Medicine and Biology Society*, IEEE, pp. 1875-1876 (1987).

Pogwizd, S. and Corr, P., "Reentrant and Nonreentrant Mechanisms Contribute To Arrhythmogenesis During Early Myocardial Ischemia: Results Using Three-Dimensional Mapping," *Circulation Research*, vol. 61, No. 3, pp. 352-371 (Sep. 1987).

Pollak, S., et al., "Intraoperative Indentification Of A Radiofrequency Lesion Allowing Validation Of Catheter Mapping Of Ventricular Tachycardia With A Computerized Balloon Mapping System," *PACE*, vol. 15, pp. 854-858 (Jun. 1992).

Potratz, J., et al., "Echocardiographic Guiding Of Catheter-Electrode During Endocardial Mapping To Determine Location Of Late Fractionated Potentials In Patients With Acute Myocardial Infarction," *European Heart Journal*, vol. 12, Abstract Supplement p. 235, abstract 1242 (Aug. 1991).

Rudy, Y. and Plonsey, R., "Annotations: A Note On 'The Brody-Effect'," *J. Electrocardiology*, vol. 11, No. 1, pp. 87-90 (1978).

Rudy, Y. and Plonsey, R., "The Eccentric Spheres Model As The Basis For A Study of The Rule Of Geometry And Inhomogeneities In Electrocardiography," *IEEE Transactions on Biomedical Engineering*, vol. BME-26, No. 7, pp. 392-399 (Jul. 1979).

Rudy, Y., et al., "The Effects Of Variations In Conductivity And Geometrical Parameters On The Electrocardiogram, Using An Eccentric Spheres Model," *Circulation Research*, vol. 44, No. 1, pp. 104-111 (Jan. 1979).

Rudy, Y. et al., "Inverse Reconstruction Of Epicardial And Endocardial Potentials: The Use Of Temporal Information," IEEE, pp. 2006-2008 (1992).

Simpson, E., et al., "Three-Dimensional Visualization Of Electrical Variables In The Ventricular Wall Of The Heart," IEEE, TH0311-1/90, pp. 190-194, (1990).

Smith, W., et al., "A Computer System for the Intraoperative Mapping of Ventricular Arrhythmias," *Computers and Biomedical Research, an International Journal*, vol. 13, No. 1, pp. 61-72 (Feb. 1980).

Smith, W. and Ideker, R., "Computer Techniques For Epicardial And Endocardial Mapping," *Progress in Cardiovascular Diseases*, vol. 26, No. 1, pp. 15-32 (Jul./Aug. 1983).

Spach, M. and Barr R., "Analysis Of Ventricular Activation And Repolarization From Intramural And Epicardial Potential Distributions For Ectopic Beats In The Intact Dog," *Circulation Research*, vol. 37, pp. 830-843 (Dec. 1975).

Stellbrink, C., et al., "Potential Of Intracardiac Ultrasonography As An Adjunct For Mapping And Ablation," *American Heart Journal*, vol. 127, No. 4, Part 2, pp. 1095-1101 (Apr. 1994).

Taccardi, B., et al., "A New Intracavitary Probe For Detecting The Site Of Origin Of Ectopic Ventricular Beats During One Cardiac Cycle," *Circulation*, vol. 75, No. 1, pp. 272-281 (Jan. 1987).

Taccardi, B., et al., "Potential Distributions And Excitation Time Maps Recorded With High Spatial Resolution From The Entire Ventricular Surface Of Exposed Dog Hearts," *Computers in Cardiology*, IEEE Computer Society Press, 0276-6547/92, pp. 1-4 (Oct. 11-14, 1992).

Tanigawa, M., et al., "Prolonged And Fractionated Right Atrial Electrograms During Sinus Rhythm In Patients With Paroxysmal Atrial Fibrillation And Sick Sinus Node Syndrome," *Journal of the American College of Cardiology*, vol. 17, No. 2, pp. 403-408 (Feb. 1991).

Tweddell, J., et al., "Potential Mapping In Septal Tachycardia: Evaluation Of A New Intraoperative Mapping Technique," *Circulation*, vol. 80 (Suppl. I), No. 3, pp. I-97-I-108 (Sep. 1989).

Witkowski, F. and Corr P., "An Automated Simultaneous Transmural Cardiac Mapping System," *American Journal of Physiology*, vol. 247, pp. H661-H668 (1984).

Young, M., et al., "A Real-Time Data Acquisition System For The Display Of Three Dimensional Cardiac Activation Maps," *Computers in Cardiology*, IEEE Computer Society Press, 0276-6547/92, pp. 331-334 (Oct. 11-14, 1992).

Yuan, S., et al., "Localization Of Cardiac Arrhythmias: Conventional Noninvasive Methods," *International Journal of Cardiac Imaging*, vol. 7, pp. 193-205 (1991).

Kristin Clingman Spencer, "*A Feasibility Study of Determining the Position of an Intracavitary Multielectrode Probe Via Impedance Measurements,* " Department of Electrical Engineering in the Graduate School of Duke University, 1991, pp. i-vii and 1-49.

Patrick Donahoe Wolf, "*Development and Evaluation of an Algorithm to Determine Boundary Geometry and Electrode Location from Impedance Measurements,*" Department of Biomedical Engineering in the Graduate School of Duke University, 1992, pp. i-viii and 1-86.

\* cited by examiner

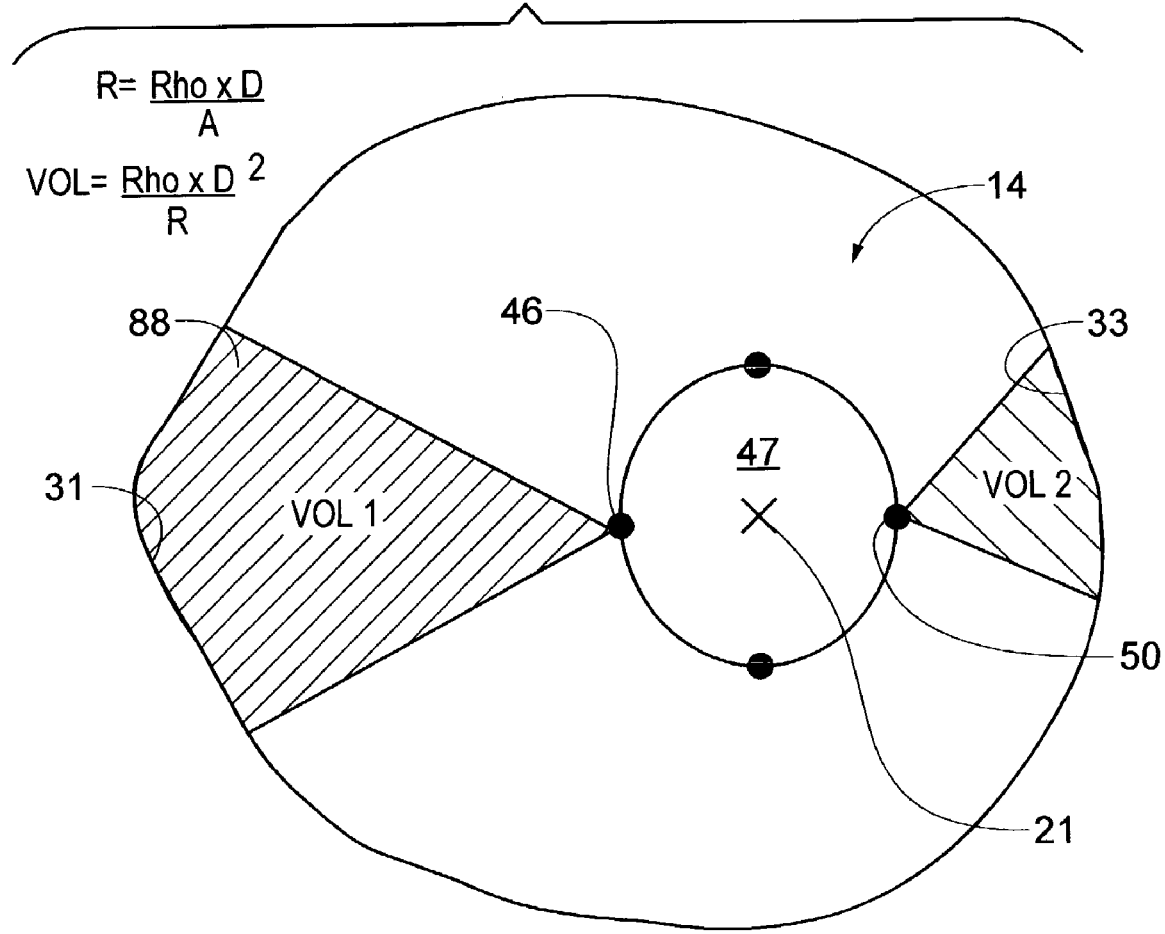

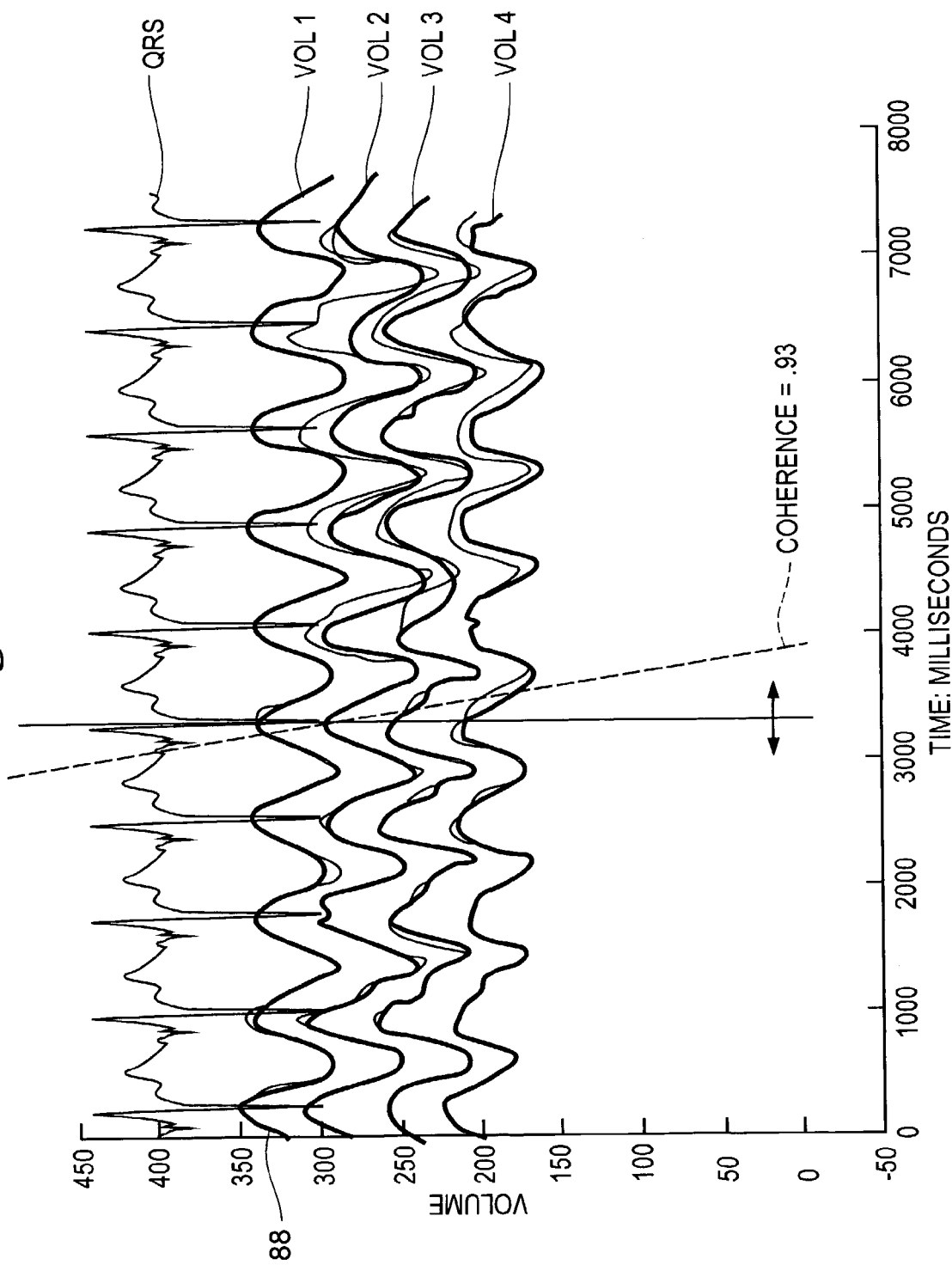

CONGESTIVE HEART FAILURE PACING OPTIMIZATION METHOD AND DEVICE

CROSS REFERENCE TO RELATED CASES

The present application is a continuation in part of U.S. patent application Ser. Nos. 09/107,371 filed Jun. 30, 1998; Ser. No. 09/589,387 filed Jun. 7, 2000; Ser No. 09/589,322 filed Jun. 7, 2000, now abandoned and 09/588,930 now U.S. Pat. No. 6,603,996 filed Jun. 7, 2000 each of which is incorporated by reference in its entirety herein. Application Ser. No. 09/588,930 is a divisional of U.S. application Ser. No. 08/387,832, filed May 26, 1995, now U.S. Pat. No. 6,240,307, which is a National Phase of PCT/US93/09015, filed Sep. 23, 1993, which is a Continuation-in-Part of U.S. application Ser. No. 07/950,448, filed Sep. 23, 1992, now U.S. Pat. No. 5,297,549, and which is a Continuation-in-Part of U.S. application Ser. No. 07/949,690, filed Sep. 23, 1992, now U.S. Pat. No. 5,311,866.

FIELD OF THE INVENTION

The present invention relates generally to cardiac pacing therapy and more particularly to biventricular pacing for the treatment of congestive heart failure.

BACKGROUND OF THE INVENTION

Congestive heart failure (CHF) is a disease state characterized by an enlargement of the heart with a concomitant reduction in pumping efficiency. Treatment regimes for CHF have included drugs, specifically diuretics, as well surgical interventions to remodel the heart. More recently it has been shown that pacing both ventricular chambers of the heart is close temporal sequence can improve the cardiac performance for CHF patients. It is believed that conduction disturbances contribute to CHF and replicating a "normal" activation sequence will improve heart function reducing or relieving symptoms.

The primary variables in biventricular pacing are the A-V delay and the V—V right and left ventricular pacing delay. In general the pacer synchronizes with the atrium and paces both ventricular chambers in sequence (V—V) after an appropriate A-V delay.

SUMMARY OF THE INVENTION

The purpose of the applicant's invention is to provide the physician with a tool to allow him to optimize the biventricular pacing therapy. The applicant proposes pacing the heart at a variety of sites in the cardiac chambers using a conventional pacing lead to survey potential sites for permanent implantation of pacing leads. During the survey the physician would have access to electrophysiological (EP) data taken on a beat-by-beat basis along with a calculated index of hemodynamic performance. In general the physician will try to maximize the hemodynamic performance based on the index of performance and then confirm that the pacing stimulus is creating an appropriate pattern of conduction with reference to the observed EP data.

The method of the invention begins with pacing the heart. This is done for several sites selected in the ventricles. This process is carried out with a pacing catheter that can be easily moved between the sites. At each site or candidate location, electrophysiologic data is collected. This data may be displayed to the physician as an activation map to show the interaction of the heart tissue with the pacing stimulus. The most typical display of data will be false color activation maps showing the propagation of the depolarization wave front over the heart as a function of time.

At each candidate pacing site, conduction volumetry is carried out with an indwelling multiple electrode array catheter such as the commercially available "ENSITE catheter" to compute volumetric changes associated with the pacing stimuli. Typically, the best cardiac performance is correlated with the most homogenous activation of the basal region of the heart chamber.

This coherence of action can be seen from the single beat activation map created with the ENSITE system. A hemodynamically based indication of coherence can be computed and expressed as a figure of merit corresponding to the homogeneity in the volume change in the chamber as the heart contracts as well. It is proposed to define and use this hemodynamic index of performance alone or together with electrical conduction measures to allow pacing optimization.

The index is based in part of the "homogeneity" or coherence of the contraction which is believed to correlate with the "vigor" of the contraction. It is preferred to compute the index on a beat-by-beat basis and to display the index of performance along with the electrophysiology data taken during the same beat. Thus the displayed data sets are from the same pacing event.

BRIEF DESCRIPTION OF THE DRAWINGS

Throughout the figures identical reference numerals refer to identical structure wherein:

FIG. 5 is a diagram of a measurement made by the system;

FIG. 6 is a display representing the "coherence" measure and the index of hemodynamic performance.

DETAILED DESCRIPTION

Theory

The disclosure is based on the collection of new data, and a new use of data presently collected within the ENSITE system as sold by Endocardial Solutions (ESI) of St Paul Minn. In this specification reference is made to patents held by ESI, each patent is incorporated by reference herein. The use of the trade marked term ENSITE is intended to refer to commercially available structures.

It has been widely known that one may pace the heart through an EP catheter or through a separate pacing catheter to explore the electrical behavior of the heart during a diagnostic or ablation procedure. More recently it has been determined that pacing in both the left and right ventricle or bi-ventricular pacing is a useful therapy for the treatment of congestive heart failure. By closely coordinating the contraction of both ventricular chambers, an improved cardiac output can be achieved which tends over time to reduce the overt symptoms of congestive heart failure. It is recently, but not widely, recognized that the timing intervals and pacing sites of biventricular pacing must be carefully selected to generate the benefits of biventricular pacing.

It is becoming well understood that the precise placement of ventricular pacing leads in the heart is critical to achieving success with biventricular pacing or other pacing therapies directed to patients with CHF. It is believed that if the lead system is located in tissue that is refractory, ischemic or scarred, the propagation of activation is delayed and the resulting contraction is disorganized and less effective than normal.

The coherence of electrical activation is a non standard but useful way of expressing the requirement that the electrical activation of the heart be propagated over the diseased tissue in a way to result in an effective contraction. From a hemodynamic viewpoint a coherent contraction arises from a homogenous volumetric contraction, in which all portion of the observable heart chamber contract progressively and in "unison".

The coherence of electrical activation can be directly observed by the ENSITE system in the EP data while the homogeneity or hydralic coherence measure is a hemodynamic index computed beat to beat by a modified ENSITE system.

Users of the ENSITE system become skilled at interrupting the propagation of such waveforms and can readily determine the location of infarcted regions in the myocardium based upon their electrical behavior. It is generally wise to avoid attempting to pace these regions of the heart.

Implementation

Figure 1:
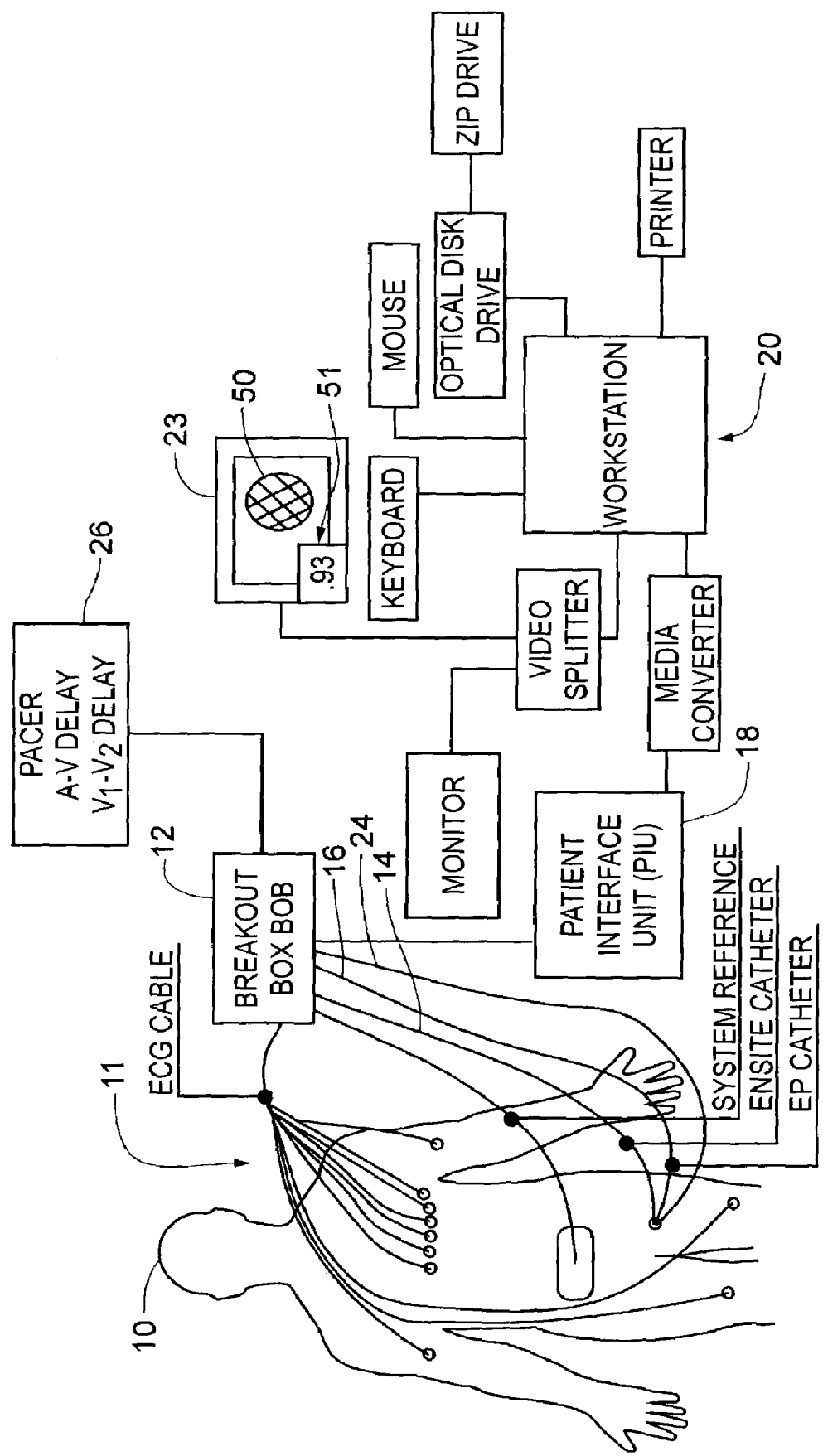
FIG. 1 is a schematic diagram of the EP system.

FIG. 1 shows a commercially available ENSITE electrophysiology mapping system sold by Endocardial Solutions of St. Paul, Minn. Although the ENSITE system in its current commercial embodiments presents electrophysiologic data on a static geometry of the heart, it should be recognized that certain heart information (EP activation) is available on a single beat basis this attribute is important in understanding the use of the system in this application.

In this system a patient 10 is undergoing a diagnostic procedure through a minimally invasive procedure involving the introduction of an ENSITE catheter coupled to the breakout box 12. A conventional electrophysiology catheter 16 is also introduced into the patient while a variety of surface electrodes 11 are used to monitor cardiac activity during the procedure. The breakout box 12 permits the ECG cables and EP system to be coupled to additional hardware, which is not shown in this figure. The patient interface unit 18 couples the ENSITE catheter to the workstation computer and its related peripherals. 20. The workstation operates under the control of a software program, which provides a substantial amount of information to the attending physician.

Figure 3:
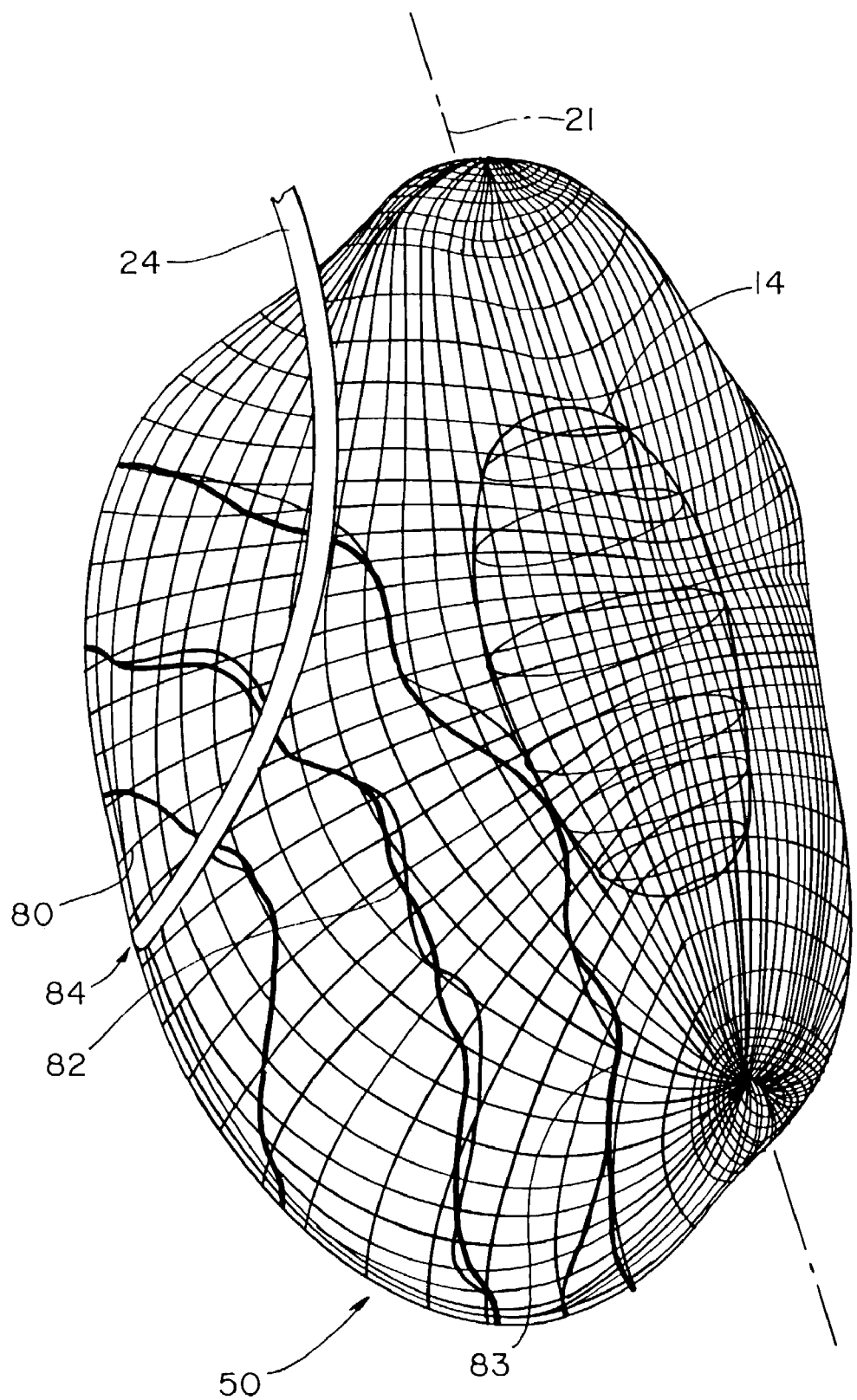
FIG. 3 is an equivalent circuit of a measurement made by the system.

In use the physician will see an activation map image similar to that shown in FIG. 3 on the monitor 23. The computed index 51 will also been shown to the physician as indicated by index value "0.93" seen on the monitor 23. In general, the physician is able to visualize the intracardiac cavity 32 containing the ENSITE catheter 14 as seen in FIG. 3 on a color monitor 23. Color is used to reduce the clutter in the image. Expressed or displayed on this wire frame geometry image 50 are activation maps and other electrophysiology information derived from the ENSITE catheter in conjunction with the EP catheter. In this particular instance, the patient is also provided with one or more pacing catheters 24 which are coupled to a temporary pacer 26 through the breakout box 12. The temporary pacer 26 allows the physician to make measurements while varying the A-V delay and the V—V delay time. Pacing rate may be varied to ensure capture.

Figure 2:
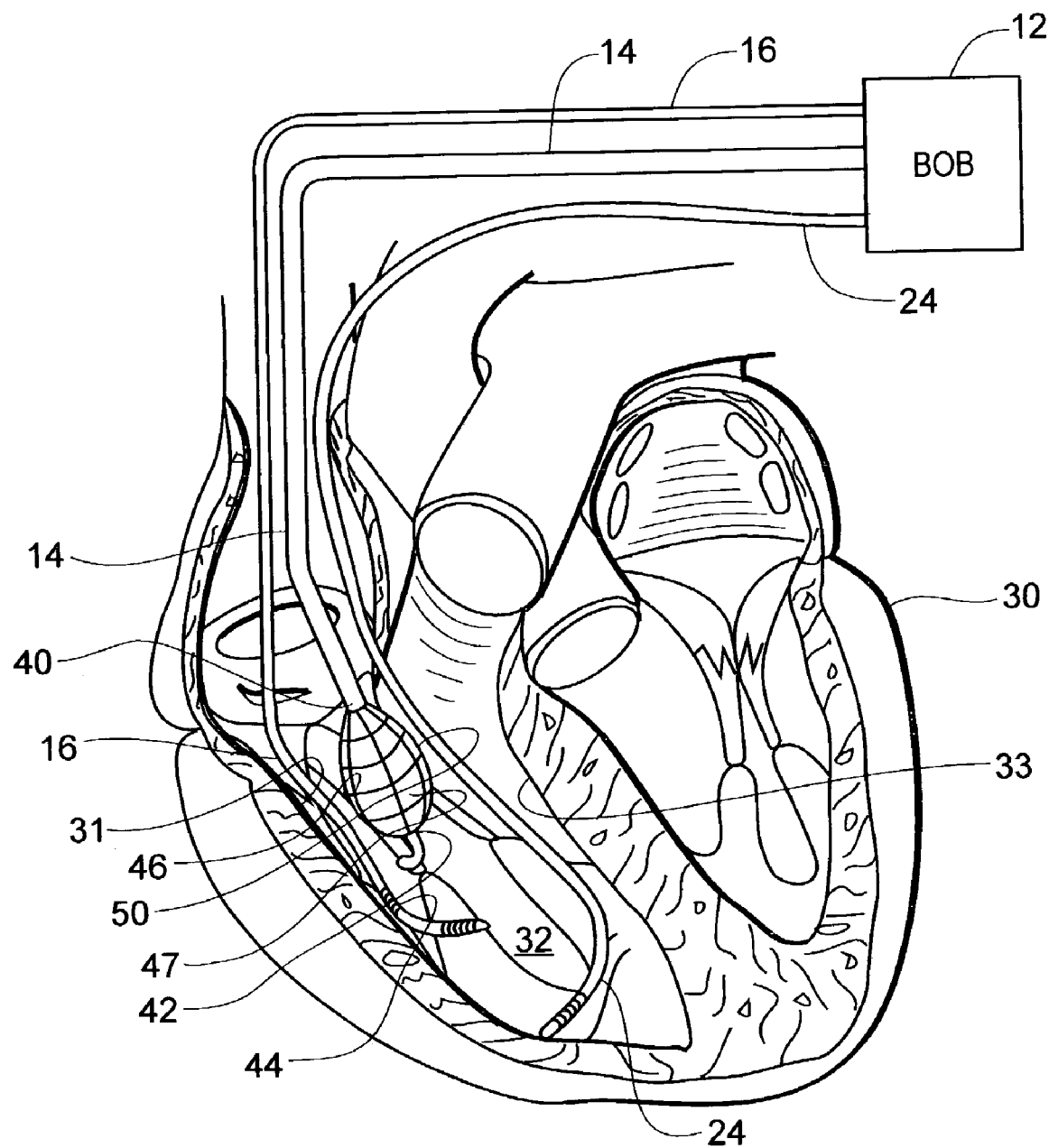
FIG. 2 is a schematic diagram of a portion of the system.

Turning to FIG. 2 the heart 30 is shown schematically with a right ventricle 32 containing the ENSITE catheter 14 and a conventional EP catheter 16 as well as the pacemaker lead 24. In brief, software running on the workstation 20 in FIG. 2 can create an electrophysiological map of the heart during a single heartbeat as follows. In operation current sourced from a pair of electrodes (electrode 40 and 42) and injected into the heart chamber 32, chamber. A roving catheter, shown as EP catheter 16, is located on the endocardial surface 31 toward the exterior of the heart this catheter may be moved widely and may be placed on the interior heart surface along the septum is shown by reference numeral 33. The injected current is detected through the electrode 44 on the EP catheter 16. This location is determined and as the catheter is moved about the chamber, complete chamber geometry can be built up by noting the sequential positions of the electrode 44. Incorporated references describe this process in more detail but for purposes of this disclosure a convex hull modeling technique is used to build a statically displayed interior geometry of the heart chamber by selecting certain locations developed from the electrode motion. The convex hull model of the interior chamber of the heart can be smoothed and a representative wire grid displayed to the physician. Such a wire grid is shown in FIG. 3 as element 50.

The ENSITE catheter also carries an array of passive electrode sites typified by electrode site 46. These electrodes are arrayed around the geometric access of the ENSITE balloon 47. At any given instant some of these electrode sites are pointed toward the exterior surface wall 31 and the septal wall 33. By computing the inverse solution, the electrophysiologic potentials passing along these surfaces can be measured within one beat. Reference may be had to U.S. Pat. Nos. 5,297,549; 5,311,866; 6,240,307 and 5,553,611 for further discussion of the inverse solution and the creation of the electrophysiologic map. Each of these references is incorporated in its entirety in the present application.

In the commercially available ENSITE system the depolarization wavefront is displayed on a representative geometric surface such as the grid surface 50 of FIG. 3. The workstation 20 animates this electrophysiology data and the propagation of the electrical way front along the interior surfaces of the heart can be monitored. Wavefronts 80 82 and 83 are sequence movements of the stimulus from pacing site 84 seen in FIG. 3.

Figure 4:
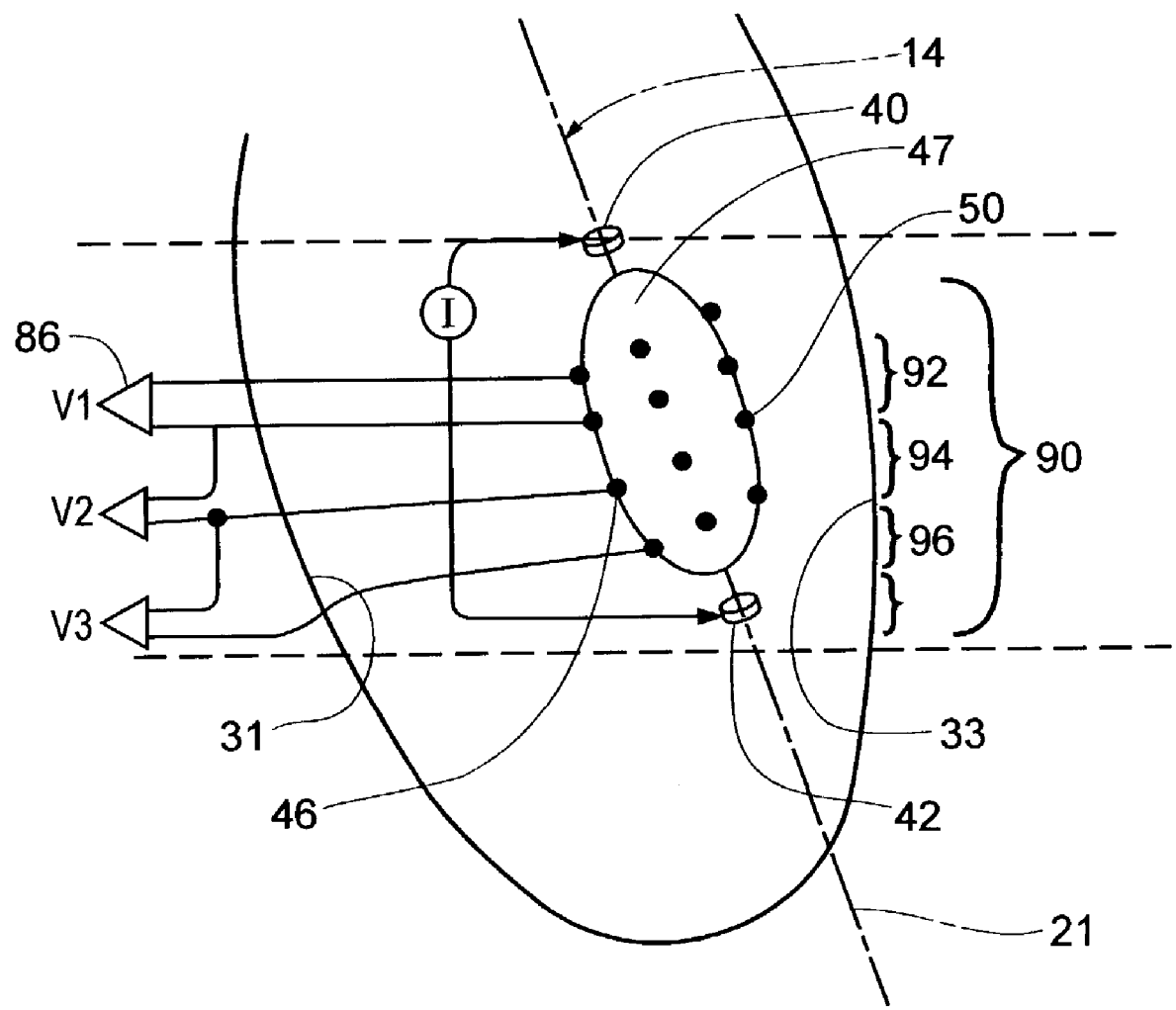
FIG. 4 is a diagram of an output display from the EP system.

FIG. 4 shows an equivalent circuit implementation to facilitate a description of conduction volumetry measurements made from an ENSITE catheter. Returning to the geometry of the array on the ENSITE catheter 14 the interior of the balloon 47 is non-conductive which provides a limited field of view for each of the electrode sites on the surface of the balloon. In essence each electrode responds only to electrical activity bounded by the heart wall, which is directly opposite the electrode site. For example, an electrode such as electrode 46 sees electrical activity and conductance data bounded by the wall 31 and is blind to electrical activity on wall 33. In a similar fashion, an electrode such as electrode 50 sees only electrical activity occurring on wall surface 33. By monitoring the voltages on the array electrodes during the pulse, or more particularly measuring the resistance between adjacent columnar pairs of electrodes as indicated by exemplary difference amplifier 86 it is possible to compute the volume of a partial slice 88 of the chamber volume best seen in FIG. 5. It is important to note that the volume measurement is segmented into several local volumes typified by volume 88.

FIG. 5 shows a slice of chamber volume computed by measuring the difference in resistance between electrodes adjacent along the axis 21. This view shows that the volume segments are non-overlapping and extend along the axis 21. The conductance term R is the resistance measured at electrodes in the passive array. This value is directly available to the software in the program, and Rho is the conductance of the blood in ohms-centimeters. D represents the distance between adjacent electrode sites in the passive array along the axis 21. This value is known from the geometry of the ENSITE catheter. The preferred conduction volumetry algorithms can be computed very fast and the volume changes throughout a single beat of the heart may be tracked. The measurement of chamber volume is most accurate at the mid volume level indicated in FIG. 4 at reference 90. It is preferred but not required to sum or stack the independent volume measurements to create "columnar values" centered on the axis 21. This is achieved by adding volumes 92 through 96 to create a column volume 90 located near the septum. A similar process is repeated to create a column volume near the wall 31 as shown as a slice 88 in FIG. 5 as well as elsewhere around the chamber.

It is believed that the most effective heartbeat will involve the simultaneous and progressive activation of all of the muscle tissue, which should result in a self similar reduction in the measured volume among all of the volume segments measured.

FIG. 6 is a display of four representative volume segments of the heart chamber displayed as a function of time. It is expected that eight volumes will be used most effectively. Segment 88 may correspond to the antero-lateral volume while the other traces represent other volumes such as the Septal; antero-septal; anterior; antero-lateral; lateral or other volumes defined around axis 21. The preferred way to compare the self-similarity of the volume waveforms is to cross correlate them statistically. By cross correlation of the values of the segment volumes over time one can compute a number that represents the similarity relationship of the various waveforms to each other. That is if the all the volumes contract identically then they should share the same waveform morphology and be completely self similar. In this instance the index value is unity. Real measurements taken have shown that a CHF patient in normal sinus rhythm has an index value of about 0.8. and that by manipulating the A-V delay time, location of stimulus and V—V delay interval this index can by increased to about 0.9 this is a very significant improvement in the heart contraction. In FIG. 6 a computed value of 0.93 is delayed showing improved contraction behavior based on the selected pacing parameters. It is important to note that it is not intended to make a display like FIG. 6 available to the physician because it is difficult to "compute" self-similarity qualitatively. The figure is designed to show how the performance index is calculated. index In operation the physician will have the index saved for each pacing location and set of pacing variables. The physician will look for an improved contraction that is reflected by a high index value and a "normal" activation sequence.

For example a relatively invariant collection of volumes on one side of the heart or the other is some indication that wall is not contracting vigorously and that a better pacing site should be selected. This coherence of contraction index can be displayed as a simple number of percent of a total (unity). It is expected that simple figures of merit will be displayed for the physician to allow him to optimize the location of the pacing lead. It is expected that a measure of hemodynamic performance based upon conduction volumetry will be given independently of a coherence of contraction index.

It must be recognized that such measures are largely arbitrary and they may be combined in a variety of ways to improve the relationship between the hemodynamic performance index and the clinical outcome for the patient based upon pacing site.

The invention claimed is:

1. A method, performed once at the time of implantation of one or more pacing leads, of optimizing a pacing site for a heart chamber of a congestive heart failure patient comprising:

pacing the heart a plurality of sites;

measuring a number of partial chamber volumes of the heart chamber over time through out one heartbeat generating a volume/time data set;

constructing a measure that compares the self-similarity of volume/time data set;

selecting the pacing conditions corresponding to the most self-similar volume time data.

* * * * *